United States Patent [19]
Toyne et al.

[11] Patent Number: 5,496,500
[45] Date of Patent: Mar. 5, 1996

[54] NAPHTHYL ORGANIC COMPOUNDS

[75] Inventors: Kenneth J. Toyne; John W. Goodby; Alexander Seed, all of Humerside; George W. Gray, Dorset; Damien G. McDonnel, Worcestershire; Edward P. Raynes, Worcestershire; Sally E. Day, Worcestershire; Kenneth J. Harrison, Worcestershire; Michael Hird, Humberside, all of England

[73] Assignee: The Secretary of State for Defence in Her Britannic Majesty's Government of the United Kingdom of Great Britain & Northern Ireland, London, England

[21] Appl. No.: 283,714

[22] Filed: Aug. 1, 1994

Related U.S. Application Data

[63] Continuation of Ser. No. 2,396, Jan. 13, 1993, abandoned.

[30] Foreign Application Priority Data

Mar. 13, 1991 [GB] United Kingdom .............. 9105359

[51] Int. Cl.$^6$ .................. C09K 19/34; C09K 19/32; G02F 1/13; C07D 333/26
[52] U.S. Cl. ................. 252/299.61; 252/299.01; 252/299.62; 359/103; 549/63; 549/83
[58] Field of Search .................... 252/299.62, 299.61, 252/299.01; 359/103; 549/29, 83, 63

[56] References Cited

U.S. PATENT DOCUMENTS 4,659,503 4/1987 Eidenschink et al. ............. 252/299.61

FOREIGN PATENT DOCUMENTS

| | | |
|---|---|---|
| WO87/06577 | 11/1987 | European Pat. Off. . |
| 0341922 | 11/1989 | European Pat. Off. . |
| 2070593 | 9/1981 | United Kingdom . |
| 1603075 | 11/1981 | United Kingdom . |

OTHER PUBLICATIONS

CA81:37427.
CA80:47707.
CA96:190717.
CA82:170509.
Patent Abstracts of Japan, vol. 10, No. 328, (C–383)(2384), 7th Nov. 1986; JP, A, 61134364 (Chisso Corp.) 21 Jun. 1986, see abstract.

*Primary Examiner*—Shean C. Wu
*Attorney, Agent, or Firm*—Nixon & Vanderhye

[57] ABSTRACT

Liquid crystal compounds of formula (I) are described, where formula (I) is given as $R_1$—A—$(X_m$—$(B)_n$—$R_2$ where A is selected from nathyl, flourinated naphthyl, brominated naphthyl, B is selected from phenyl, methylated phenyl, brominated phenyl, fluorinated phenyl, thiophene, pyrimidine and pyridine, $R_1$ and $R_2$ are independently selected from alkyl, alkoxy, alkynyl, thioalkyl, Br, CN, SCN, NCS, perfluoroalkyl, perfluoroalkoxy and hydrogen, X is selected from C≡C, COO and C=C, m is 0 or 1, n is 0 or 1 where m is 1 and n is 0 where m is 0; provided that where A is naphthyl, n is 1 and m is 0 then B is selected from methylated phenyl, brominated phenyl, thiophene, pyrimidine and pyridine; and further provided that where A is naphthyl, X is C≡C, m is 1 and n is 1, then B is selected from thiophene, pyrimidine and pyridine. Also described are liquid crystal compounds suitable for inclusion in devices utilizing pretransitional characteristics of liquid crystalline materials in the isotropic phase and described by formula (II): $R_3$—J—$(Y)_p$—$(Z)_q$—$R_4$, where J is selected from nathyl, fluorinated naphthyl, brominated naphthyl, Z is selected from phenyl, methylated phenyl, brominated phenyl, fluorinated phenyl, thiophene, pyrimidine and pyridine, $R_1$ and $R_2$ are independently selected from alkyl, alkoxy, alkynyl, thioalkyl, Br, CN, SCN, NCS, perfluoroalkyl, perfluoroalkoxy and hydrogen, Y is selected from C≡C, COO and C=C, p is 0 or 1, q is 0 or 1 where p is 1 and q is 0 where p is 0.

16 Claims, 5 Drawing Sheets

NAPHTHYL ORGANIC COMPOUNDS

This is a continuation of U.S. application No. PCT/GB92/00411, filed Mar. 9, 1992. This is a continuation of U.S. application Ser. No. 08/002,396, filed Jan. 13, 1993, now abandoned.

This invention relates to compounds containing a naphthyl group and which have liquid crystalline properties and/or which are suitable for use as constituents of liquid crystal materials. The invention also relates to use of such compounds in liquid crystal materials.

Liquid crystal materials and devices exploit the electro-optical properties of nematic and cholesteric (N or N*), or smectic (S) with particularly useful smectic phases being chiral smectic C ($S_C^*$) or smectic A.

Liquid crystal materials which show ferroelectric $S_C^*$ phase are useful in fast switching displays such as television or VDU screens as the $S_C^*$ phase can be switched in a few milliseconds or even microseconds. The principle of $S_C^*$ switching is described inter alia by N A Clark and S T Lagerwall in App Phys Lett 36 (1980) p899.

Materials which show an $S_A$ liquid crystal phase may be used in display devices which exploit the electroclinic effect.

The use of liquid crystal materials to exhibit electro-optical effects in displays and other optical devices such as digital calculators, watches, meters and alphanumeric laptop computers is now well known. However, known liquid crystal materials are not ideal in all respects and a considerable amount of work is currently being carried out in the art to improve their properties.

Liquid crystal materials normally consist of specially selected mixture compositions and improved materials are often obtained by forming new mixtures having an improved combination of properties.

The composition of liquid crystal mixture is generally selected so that the mixture shows desirable properties. In particular such properties include:

(1) a liquid crystalline temperature range—including room temperature (20° C.)—which is as wide as possible;
(2) a melting point (solid-to-liquid crystal transition temperature) which is as low as possible;
(3) a clearing point (liquid crystalline to isotropic liquid transition temperature) which is as high as possible;
(4) a positive or negative (as appropriate) dielectric anisotropy (permittivity measured parallel to the molecular axis less that measured perpendicular to the molecular axis) which is as great as possible in order to minimize the display voltage;
(5) a viscosity which is as low as possible in order to minimize the display switching speeds;
(6) an electro-optical response which varies as little as possible with temperatures;
(7) a good chemical and photochemical stability;

Examples of further particular properties useful in specific applications include:

(8) a good multiplexability;
(9) an ability to switch dielectric anisotropy with frequency;
(10) a birefringence of selected magnitude;
(11) specific elastic constants which can be tailored to meet specific device requirements; and
(12) high electrical resistivity for certain applications.

Liquid crystal materials and devices exploit the electro-optical properties of nematic or cholesteric (N and N* respectively), or smectic (S) in particular chiral smectic C ($S_C^*$) or smectic A ($S_a$) phase. The most common type of liquid crystal materials in use are those which show a nematic phase and these are extensively used in, for example, watches, clocks, calculators, electronic displays etc.

For some applications of liquid crystal materials a high birefringence is sought, e.g. in so called "electrically controlled birefringence" (ECB) effect devices (see, for example, M F Schieckel and K Fahrensohn Applied Physics Letters 19 p2912 1971), in thin film transistors and supertwisted nematic devices. It is rare for the requisite desirable properties to be found in a single liquid crystalline compound and generally liquid crystalline materials consist of mixtures of component compounds. Very many liquid crystalline compounds suitable for such uses are known and will be apparent to those in the art.

Some liquid crystalline compounds based on the phenyl-naphthalene system are known e.g.

For example, Bull Soc Chim Fr 11–12(2) p2521–2426 (1975) describes compounds where A is alkoxy and B is alkyl or alkoxy, and Helv Chim Acta 68(5) p1406–1426 describes those in which a is alkyl or alkoxy and B is cyano or trifluoromethyl.

It is the aim of this invention to provide novel compounds which provide improved or alternative liquid crystalline and/or monotropic characteristics.

According to this invention, liquid crystal naphthyl compounds of formula I are provided;

Formula I where A is selected from nathyl, fluorinated naphthyl, brominated naphthyl, B is selected from phenyl, methylated phenyl, brominated phenyl, fluorinated phenyl, thiophene, pyrimidine and pyridine, $R_1$ and $R_2$ are independently selected from alkyl, alkoxy, alkynyl, thioalkyl, Br, CN, SCN, NCS, perfluoroalkyl, perfluoroalkoxy and hydrogen, X is selected from C≡C, COO and C=C, m is 0 or 1, n is 0 or 1 where m is 1 and n is 0 where m is 0;
provided that
where A is naphthyl, n is 1 and m is 0 then B is selected from methylated phenyl, brominated phenyl, thiophene, pyrimidne and pyridine;
and further provided that
where A is naphthyl, X is C≡C, m is 1 and n is 1, then B is selected from thiophene, pyrimidine and pyridine.

The preferred embodiments of the invention discussed below are inter alia chosen with respect to their liquid crystalline properties, particularly with respect to suitability for use in high birefringence nematic or ferro-electric Sc* liquid crystal materials. Preferably for use in nematic materials alkyl, alkoxyl, thioalkyl and alkynyl substituents $R_1$ and $R_2$ contain 1–15 carbon atoms, and more preferably contain 1–5 carbon atoms for use as nematic materials and 3–9 carbon atoms for use as smectic materials. Preferably for smectic C materials $R_1$ and $R_2$ are selected from n-alkyl or n-alkoxy.

According to a further aspect of this invention compounds suitable for inclusion in devices utilizing pretransitional characteristics of liquid crystalline materials in the isotropic phase are provided, of general Formula II

$R_3$—J—$(Y)_p$—$(Z)_q$—$R_4$   Formula II where J is selected from nathyl, fluorinated naphthyl, brominated naphthyl, Z is selected from phenyl, methylated phenyl, brominated phenyl, fluorinated phenyl, thiophene, pyrimidine and pyridine, $R_1$ and $R_2$ are independently selected from alkyl, alkoxy, alkynyl, thioalkyl, Br, CN, SCN, NCS, perfluoroalkyl, perfluoroalkoxy and hydrogen, Y is selected form C=C, COO and C≡C, p is 0 or 1, q is 0 or 1 where p is 1 and q is 0 where p is 0;

Typically such compounds can be utilized in devices such as Optical Kerr Effect devices. Such devices are often used as optical shutters or optical modulators, and rely on the fact that birefringence (Δn) of a medium being proportional to the square of an applied electric field. Such an effect is often termed the quadratic electro-optic effect and can be investigated using degenerate four wave mixing (P Madden et al. IEEE J of Quantum Electronics QE22 No 8 Aug. 1986 p1287).

Preferably where $R_3$ and $R_4$ are selected from $C_{1-15}$ alkyl, alkoxy, thioalkyl and alkynyl; more preferably $C_{1-9}$ and even more preferably $C_{3-9}$.

Preferred overall structures of formula I and formula II are now listed:

1.1

1.2

1.3

1.4

1.5

1.6

1.7

1.8

Naphthyl materials of formula I and formula II may be generally prepared by various routes which will be apparent to those in the art. Typical routes which can be used include reaction of an appropriate phenyl (or equivalent e.g. thiophene, pyrimidine etc.) boronic acid with an appropriate naphthol triflate. Alternatively, an appropriate boronic acid can be reacted with such appropriate compounds as bromonitro- e.g. acid can be reacted with such appropriate compounds as bromonitro- e.g. appropriate benzene, thiophene residues etc., for CN and NCS terminal groups. Terminal groups of alkyls, alkoxys, alkynyls and thioalkyls can be achieved by well known alkylation, 0-alkylation, alkynylation (via appropriate triflate) and thioalkylation routes respectively. Naphthyl materials of where m and n are 0 can be prepared from bromonaphthol by using e.g. alkylation, thioalkylation etc., and also be followed by e.g. cyanation (by use of e.g. CuCN) etc.

The invention also provides a liquid crystal material being a mixture of at least two compounds, at least one of which is a naphthyl compound of formula I. This material may show a nematic or smectic (e.g. $S_a$, $S_c^*$ or $S_c$) characteristics and also sometimes isotropic properties.

In particular many naphthyl compounds of formula I have a high anisotropy in polarisability (Δa), making them suitable for applications in which this characteristic is required, as discussed above. Naphthyl compounds of formula I may be used as components of nematic liquid crystal materials together with other liquid crystalline compounds, for example compounds of general formula III:

$R_1$—X—$[C=C]_m$—$[C≡C]_n$—$[Y]_p$—$R_2$   Formula III $R_1$ is selected from a group comprising hydrogen, alkyl, alkoxy, alkynyl, thioalkyl, CN, and Br; $R_2$ is selected from a group comprising hydrogen, NCS, SCN, CN, alkyl, alkoxy, alkynyl, and thioalkyl; m and n are 1 or 0 such that m is 1 where n is 0 and m is 0 where n is 1 or 0; p is independently 1 or 0; X is selected from a group comprising of naphthyl, fluorinated naphthyl and brominated naphthyl; and Y is selected from a group comprising of phenyl, methylated phenyl, brominated phenyl, thiophene and pyrimidine and pyrindine.

The mixture may also contain such materials as phenyl thiazolenes of typical structure such as that seen in Formula IV Formula IV where typically $R_3$ is CN, alkyl, alkoxy etc.

Other suitable mixture materials include for example those of materials described in U.S. application No. 892828.6, where their use as polymer network materials suitable for e.g. dispersion within a matrix of transparent polymer is described.

The mixture may also contain one or more fluorinated cyanobiphenyls or terphenyls of formula V:

Formula V where $R_1$ is $C_{1-10}$ n-alkyl or n-alkoxyl and the fluorosubstituent(s) may be in any one or two of the available substitution positions. Compounds of the formula V are known (PCT/GB 89/00647) and with their inclusion in mixture, it is possible to further increase birefringence.

A nematic liquid crystal of this invention may also contain one or more optically active compounds to induce a cholestric phase and one or more pleochroic dyes.

The materials of this aspect of the invention may be used in any of the known forms of liquid crystal display devices, for example a twisted nematic device, Freedricks effect device, cholesteric memory mode device, cholesteric to nematic phase change effect device, dynamic scattering effect device two frequency switching effect device, a supertwist effect device, or a thermometer using a thermochromic material. The method of construction and operation of such devices, and characteristics of a liquid crystal material suitable for use therein, are well known in the field. Typically an electro-optical display device will consist of 2 substrates between which a layer of the liquid crystal material may be sandwiched. At least one of the substrates is optically transparent and both have addressable electrodes which are preferably made of a transparent material on their opposing faces. By applying an electric field across the layer of liquid crystal material via the electrodes an electro-optical effect is achieved which may be viewed directly or preferably through one or more polarizing filters.

Another aspect of the invention is a material, being a mixture of compounds, characterized in that the mixture is suitable for inclusion in devices utilizing pretransitional characteristics of liquid crystalline mixtures in the isotropic phase and that the mixture includes at least on compound of formula II. Such materials also contain compound(s) of formula III and/or compound(s) of formula IV and/or compound(s) of formula V.

Compounds of formula II and also materials including compound(s) of formula II may be used in devices that utilize the optical Kerr Effect. Typically optical Kerr effect devices comprise a glass cell containing two electrodes, where the glass cell is filled with a polar liquid. The device is frequently termed a Kerr cell. The Kerr cell can be positioned between two crossed polarizers having transmission axes at ±45° to an electric field applied across the Kerr cell. With zero voltage applied across the Kerr cell no light will be transmitted and the cell operates as a closed shutter. Application of a modulating voltage generates a field causing the Kerr cell to function as a variable wave plate and thus operating the Kerr cell as a shutter capable of opening proportionately to the applied field.

Nematic materials of this invention may be particularly suitable for use in ECB effect devices, due to the high birefringence of the materials. They may also be particularly suitable for use in polymer dispersed liquid crystal (PDLC) materials in which small droplets of a liquid crystal material are dispersed within a matrix of a transparent polymer.

Non-limiting examples illustrating this invention will now be described with reference to the accompanying figures, of which FIGS. 1 to 5 schematically show synthetic routes for exemplified compounds 1 to 5.

EXAMPLE 1

Figure 1:
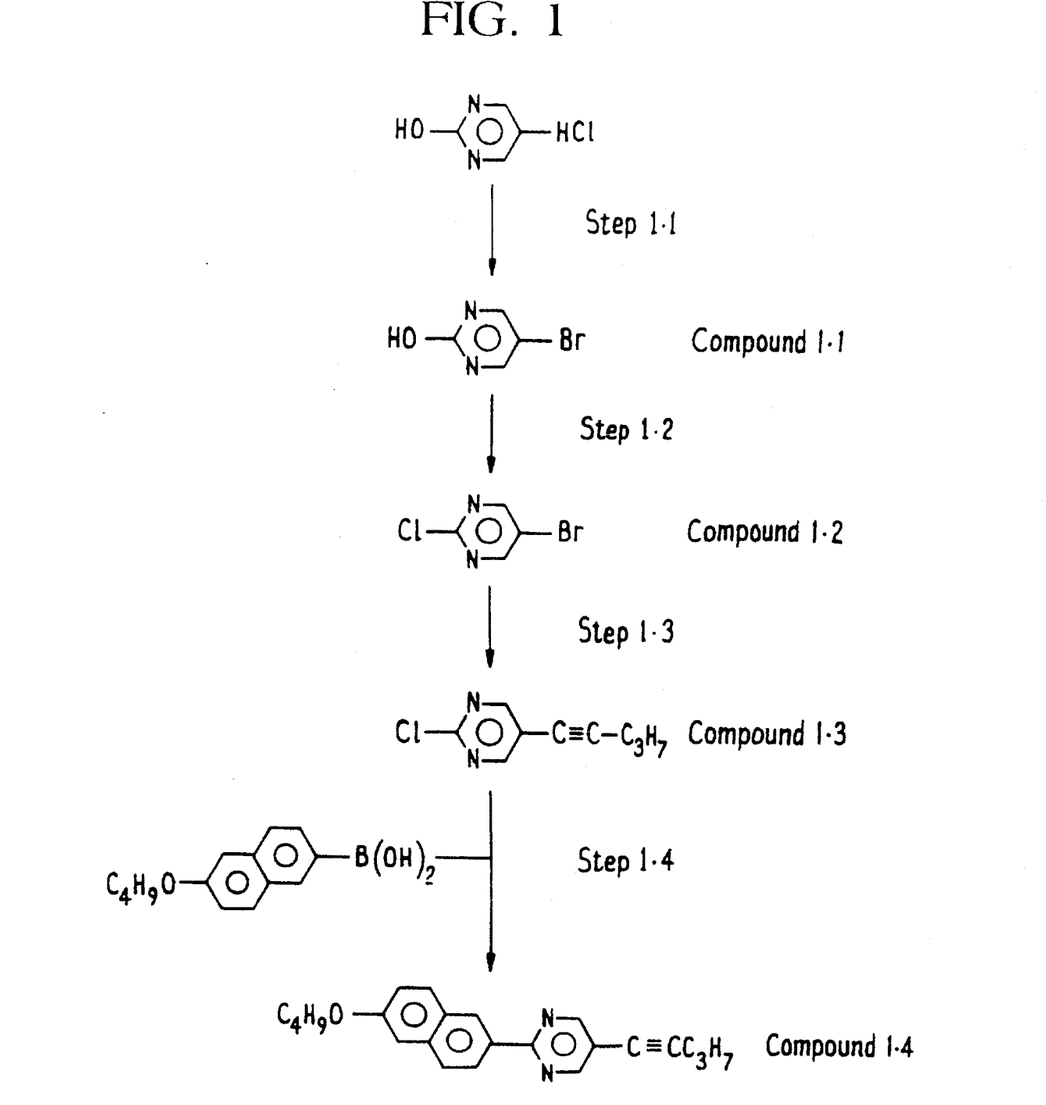

Preparation of:

With reference to FIG. 1 it can be seen that

Step 1.1 5-Bromo-hydroxypyrimidine

Bromine (67.00 g, 0.419 mol) is added slowly dropwise to a stirred solution of 2-hydroxypyrimidine hydrochloride (50.00 g, 0.377 mol) in water (200 ml) at room temperature (exothermic reaction but no cooling used). The solution is stirred for 1 hour (until cool) and then water and excess bromine is removed in vacuo to give a pale yellow solid which is dried in vacuo (0.1 mmHg) giving 5-Bromo-2-hydroxypyrimidine as a solid which is still "wet" as a yield of 100 g.

Step 1.2 5-Bromo-2- chloropyrimidine

A solution of compound 1.1 (assume 100% yield from previous preparation; 65.98 g, 0.377 mol) in phosphorous oxychloride (500 ml) and N,N-dimethylaniline (20 ml) is heated under reflux for 4 hours, the cooled mixture is carefully poured onto ice and extracted into ether (×2). The combined etheral extracts are washed with aqueous sodium hydrogen carbonate and dried ($MgSO_4$). The solvent is removed in vacuo to yield an off-white solid. Yield (based on 2-hydroxypyrimidine hydrochloride) is 23.55 g. 32%.

Step 1.3 2-Chloro-5-pent-1-ynylpyrimidine

Quantities: pent-1-yne (3.00 g, 0.044 mol), n-butyllithium (4.40 ml, 10.0 M in hexane, 0.044 mol), zinc chloride (6.00 g, 0.044 mol), compound 1.2 (8.00 g, 0.041 mol), tetrakis (triphenylphosphine)palladium(0) (1.5 g, 1.30 mol).

This experimental procedure is a zinc coupling reaction. The n-butyllithium solution is added dropwise to a stirred, cooled (−5° C. to 0° C.) solution of the pent-1-yne in dry THF under dry nitrogen. This mixture is stirred for 10 minutes and then a solution of the zinc chloride (dry) in dry THF is added dropwise at about −5° C. to 0°. The mixture is stirred at room temperature for 15 minutes and a solution of compound 1.2 in dry THF is added dropwise at −5° C. to 0° C. followed by addition of the tetrakis (triphenylphosphine)palladium(0), the mixture is heated under reflux for 22 hours (glc analysis revealing a complete reaction). The crude product is purified by column chromotography [silica gel/ petroleum fraction (bp40°–60° C.)- dichloromethane, 1:20] to give a colorless solid which is crystalized from hexane to yield colorless crystals. Yield is 6.27 g (85%).

Step 1.4 2-butoxy-6-(5-pent-1-ynylpyrimidine-2-yl)naphthalene

Quantities: compound 1.3 (1.60 g, 8.86 mol), 6-butoxynaphth-2-ylboronic acid (2.60 g, 0.011 mol), tetrakis(triphenylphosphine)palladium(0) (0.35 g, 0.03 mol).

This experimental procedure is a boronic acid coupling reaction. A solution of the boronic acid in dimethoxyethane is added to a stirred mixture of compound 1.3 and tetrakis(triphenylphosphine)palladium(0) in dimethoxymethane and 2M sodium carbonate at room temperature under dry nitrogen. The mixture is heated under reflux for 18 hours (glc analysis revealing a complete reaction). The crude product is purified by column chromatography [silica gel/ petroleum fraction (bp40°–60° C.)- dichloromethane, 1:2] to give a colorless solid which is recrystallized from ethyl acetate-ethanol (1:1) to yield colorless crystals. Yield is 2.25 g (74%).

EXAMPLE 2

Figure 2:
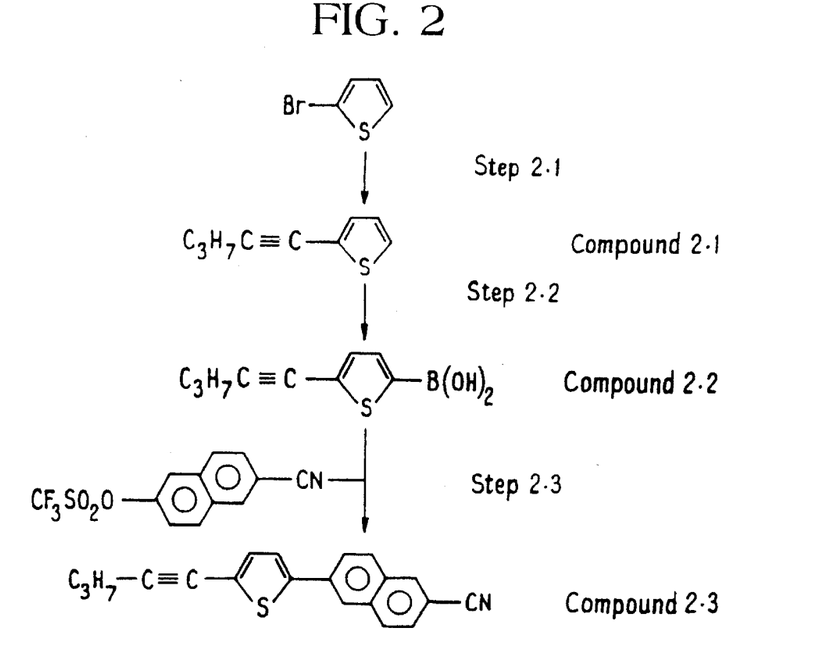

Preparation of:

With reference to FIG. 2 it can be seen that
Step 2.1 2-pent-1-ynylthiophene
Quantities: pent-1-yne (6.80 g, 0.10 mol), n-butyllithium (10.0 ml, 10.0 M in hexane, 0.044 mol), zinc chloride (13.60 g, 0.10 mol), 2-bromothiophene (16.00 g, 0.098 mol), tetrakis (triphenylphosphine)palladium(0) (3.40 g 2.94 mol).

The experimental procedure is as described for step 1.3. The crude product is distilled to yield a colorless liquid. Yield is 12.96 g (88%).
Step 2.2 5-pent-1-ynylthiophen-2-ylboronic acid
Quantities: compound 2.1 (10.00 g, 0.067 mol), n-butyllithium (6.80 g, 10.0 M in hexane, 0.068 mol), trimethyl borate (14.20 g, 0.137 mol). This experimental procedure is a standard boronic acid preparation and yields a brown solid. The yield is 12.00 g (93%).
Step 2.3 2-(6-Cyanonaphth-2-yl)-5-pent-1-ylthiophene
Quantities: 6-cyanonaphth-2-yl triflate (2.00 g, 6.64 mol), 5-pent-1-ynylthiophen- 2-ylboronic acid (1.55 g, 7.99 mmol), tetrakis (triphenyl phosphine)palladium(0) (3.40 g 2.94 mol), lithium chloride (0.85 g, 0.020 mol).

This experimental procedure is as for the boronic acid coupling reaction described in step 1.4, except for the addition of lithium chloride as a catalyst. The crude product is purified by column chromotography [silica gel/petroleum fraction (bp 40°–60 ° C.)- dichloromethane, 1:1] to give a yellow solid, which is recrystallized from ethanol to yield pale yellow crystals. Yield is 1.55 g (78%).

EXAMPLE 3

Figure 3:
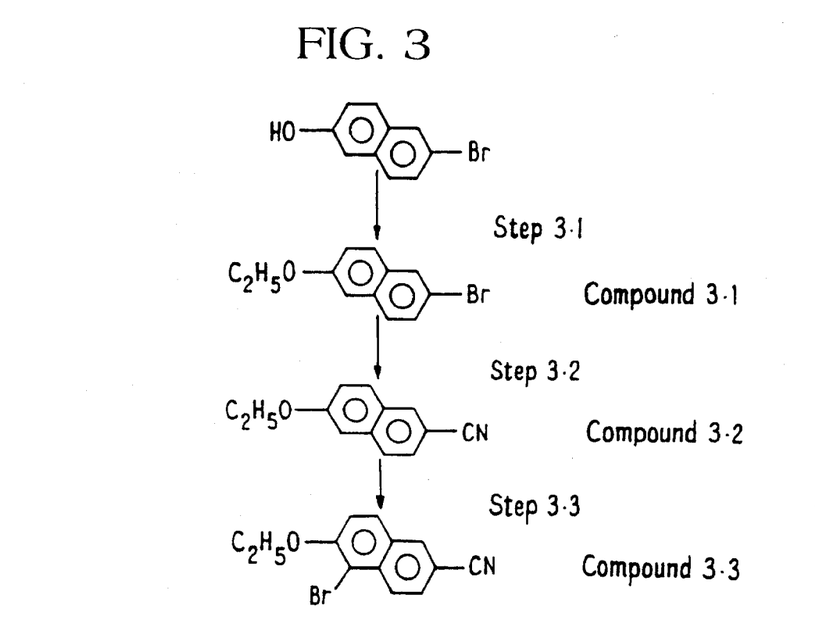

Preparation of:

With reference to FIG. 3 it can be seen that
Step 3.1 2-Bromo-6-ethoxynaphthalene
This experimental procedure is an 0-alkylation. A solution of bromomethane (48.90 g, 0.45 mol) is added dropwise to a stirred refluxing mixture of 6-Bromo-2-naphthol (40.00 g, 0.18 mol) and potassium carbonate (63.00 g, 0.46 mol) in acetone. The stirred mixture is heated under reflux for 24 hours (i.e. until glc analysis reveals a complete reaction. The potassium carbonate is filtered off, water is added to filtrate and the product is recrystallized from ethanol to give a yield of 43.92 g (97%).

Step 3.2 2-Ethoxy-6-cyanonaphthalene
This experimental procedure is a cyanation where compound 3.1 (3.00 g, 0.012 mol) is reacted with Copper (I) cyanide (1.30 g, 0.015 mol), with the crude product purified by column chromatography [silica gel/petroleum fraction (bp 40°–60° C.)- dichloromethane, 1:2) to give a colorless solid which is distilled [Kugeklrohr, 170° C. (maximum) at 0.1 mmHg] to yield 1.75 g (74%) of colorless solid.
Step 3.3 1-Bromo-6-cyano-2-ethoxnaphthalene
A solution of bromine (1.72 g, 0.011 mol) in glacial acetic acid (4 ml) is added dropwise to stirred solution of compound 3.2 (1.93 g, 9.80 mol) in glacial acetic acid (35 ml) at 80° C. The solution is stirred for an additional 10 minutes (glc revealing a complete reaction and only one product peak). The solution is added to water and the product is extracted from ether (×2) and the combined ethereal extracts are washed with water and sodium methabisulphite and dried. The solvent is removed in vacuo and the residue purified by column chromotography [silica gel/petroleum fraction (bp 40°–60° C.)- dichloromethane, 1:1] to give a colorless solid (1.72 g) which is recrystallized from hexane-dimethoxymethane (1:1) to yield 1.55 g (57%) colorless crystals.

EXAMPLE 4

Preparation of

Figure 4:
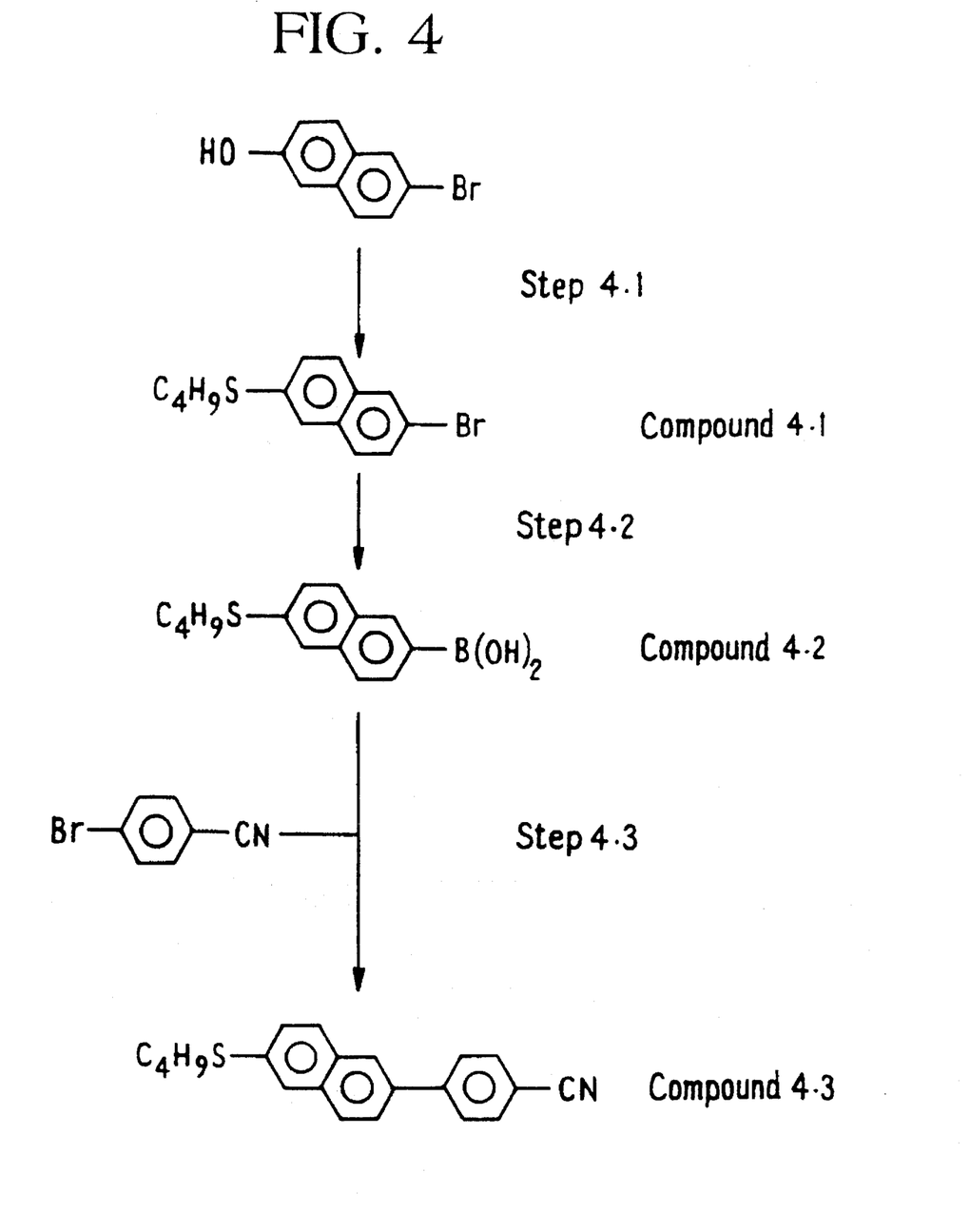

With reference to FIG. 4 it can be seen that
Step 4.1 2-Bromo-6-thiobutylnaphthalene
Trifluoromethanesulphonic acid (14.85 g, 0.099 mol) and butanethiol (8.07 g, 0.090 mol) in dry benzene (180 ml) under dry nitrogen. The resulting solution is stirred at 50° C. for 4 hours (glc analysis revealing a complete reaction), cooled and poured into ice-cold water. The product is extracted into ether (×2), the combined organic phases washed with 5% sodium hydroxide and water and dried (MgSO$_4$). The solvent can the be removed in vacuo and the residue distilled to give a colorless solid. Yield is 13.80 g (52%).
Step 4.2 6-Thiobutylnaphth-2-ylboronic acid
Quantities: compound 4.1 (6.80 g, 0.023 mol), n-butyllithium (2.30 ml, 10.0 M in hexane, 0.023 mol), trimethylborate (4.80 g, 0.046 mol). This experimental procedure is a preparation of the appropriate boronic acid by standard procedures, giving a yield of 3.49 g (58%) after the product of the reaction is extracted into 10% potassium hydroxide, the basic extract washed with ether and acidified, extracted into ether and dried (MgSO$_4$), and removal of solvent in vacuo to give a colorless liquid.
Step 4.3 2-(4-Cyanophenyl)-6-thiobutylnaphthalene
Quantities: compound 4.2 (1.81 g, 6.96 mol), 4-bromobenzonitrile (1.15 g, 6.32 mol), tetrakis(triphenylphosphine)palladium(0) (0.235 g, 0.22 mol).

This experimental procedure is a boronic acid coupling reaction as previously described in step 1.4, followed by purification of the crude product by column chromatography [silica gel/petroleum fraction (bp 40°–60° C.)- dichloromethane, 1:1] to give a colorless solid which is then recrystallized from ethanol-ethyl acetate (4:1) to yield 1.63 g (81%) of colorless crystals.

EXAMPLE 5

Preparation of

Figure 5:
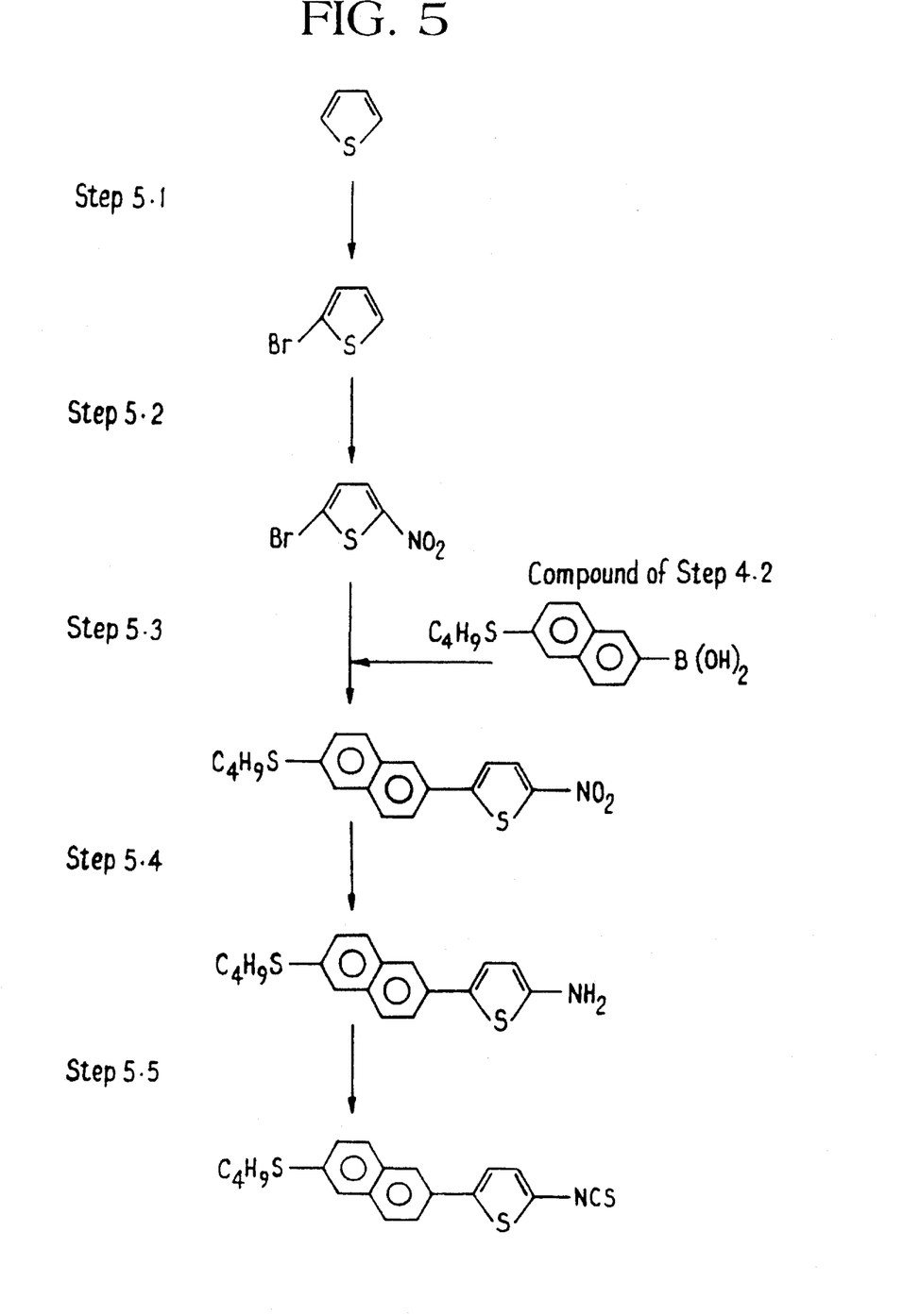

With reference to FIG. 5 it can be seen that

Step 5.1 2-Bromothiophene

A solution of thiophene (31.88 g, 0.380 mol) and N-bromosuccinimide (64.00 g, 0.360 mol) in a mixture of chloroform (80 ml) and glacial acetic acid (80 ml) was heated under reflux (with stirring) for 0.5 hours (constant glc analysis revealed a complete reaction with minimal formation of 2,5-dibromothiophene). The reaction mixture was diluted with water and washed with dichloromethane (2×100 ml); the combined organic extracts were washed successively with water (300 ml) and aqueous potassium hydroxide (5%, 300 ml) before being dried (MgSO$_4$). The solvent was removed in vacuo and the residue was distilled to give a colorless liquid.

Yield 24.34 g (42%).

Step 5.2 2-Bromo-5-nitrothiophene

Nitric acid (24.00 g, 1.42 sp gr, 0.381 mol) in acetic anhydride (50 ml) at 0° C. was added dropwise to a cooled (0° C.) rapidly stirred solution of the compound of step 5.1 (24.77 g, 0.152 mol) in acetic anhydride (50 ml). At the end of the addition the stirring was continued for 0.5 hr and the mixture was refrigerated overnight. The mixture was poured into ice water (400 ml) and the precipitate was filtered off, dissolved in ether (2×200 ml), and washed with water until free of acid. The solvent was removed in vacuo and the residue was purified by column chromatography [silica gel/petroleum fraction (bp 40°–60° C.), dichloromethane, 5:1] and was recrystallized from ethanol/dimethoxyethane, 100:1 to give a pale yellow solid which was dried in vacuo (P$_2$O$_5$) to give 66% yield of 20.89 g.

Step 5.3 2-(6-Thiobutyl-2-naphthyl)-5-nitrothiophene

Quantities: Compound of step 4.2 (4.00 g, 0.015 mol), compound of step 5.2 (3.31 g, 0.016 mol), tetrakis (triphenylphosphine)palladium(0) (0.910g, 0.001 mol), sodium carbonate (15.8 ml, 2.0 M, 0.03 mol).

The compound of step 5.2 was added all at once to a rapidly stirred mixture of the palladium catalyst, the compound of step 4.2, and aqueous sodium carbonate solution in dimethoxymethane under dry nitrogen. The reaction mixture was refluxed overnight (tlc and glc revealed a complete reaction) and the product was extracted into ether; the combined ethereal solutions were washed with saturated sodium chloride solution and dried (MgSO$_4$). The solvent was removed in vacuo and the product was purified by column chromatography [silica gel/petroleum fraction (bp 40–60), dichloromethane, 5:1] to give an orange solid with a 71% yield (3.41 g).

Step 5.4 2-(6-thiobutyl-2-naphtyl)-5-aminothiophene

A stirred solution of compound of step 5.3 (2.62 g, 0.008 mol) and palladium on carbon (10%, 2.22 g) in ethanol and tetrahydrofuran was stirred under hydrogen overnight. The catalyst was removed by filtration through "Hyflo supercel" and the solvent was removed in vacuo to afford a black solid which was used in the next step without purification after yielding 2.39 g (100%), purity (glc) 50%.

Step 5.5 2-(6-thioputyl-2-naphthyl)-5-isothionatothiophene

A solution of compound of step 5.4 (2.30 g, 0.007 mol), in chloroform was added to a stirred, cooled (0°–5° C.) solution of calcium carbonate (1.17 g, 0.012 mol) and thiophosgene (0.97 g, 0.008 mol) in water and chloroform at 0°–5° C. The mixture was heated at 35° C. for 1 h (glc and tlc analysis confirmed a complete reaction) and poured into water. The organic layer was washed with hydrochloric acid (1%, 100 ml) and dried (MgSO$_4$). The compound was purified by column chromatography [silica gel/petroleum (bp 40°–60° C.), dichloromethane, 5:1] and was recrystallized to give 0.57 g (22% yield) of a pale green solid which was dried in vacuo (CaCO$_3$), having an indicated (hplc) purity of >99%.

Liquid crystal transition temperatures between crystalline (K), nematic (N), smectic B (S$_B$) and isotropic (I) are given in Table 1 below for compounds of Formula I and Formula II. The table also contains a comparison of anisotropy in polarisability Δa with that of 4-cyano-(4'pentyl)-1-phenylcyclohexane (5PCH) and the birefringence (Δn) of the compounds. [ ]denotes a virtual phase transition.

TABLE 1

| COMPOUND | PHASE TRANSITION TEMPS (°C.) | Δa | Δn |
|---|---|---|---|
|  | K 146 [N 136.5] I | | |
|  | K 84 [79.5] I | | 4.88 |

TABLE 1-continued

| COMPOUND | PHASE TRANSITION TEMPS (°C.) | Δa | Δn |
|---|---|---|---|
| [CN-naphthalene(Br)-OC₂H₅] | K 163.5 [N 79.5] I | 1.41 | |
| [C₄H₉S-naphthalene-phenyl-CN] | K 92 [N 107] I | 4.11 | |
| [C₄H₉S-naphthalene-thiophene-NCS] | | | 0.405 |
| [C₄H₉S-naphthalene-CO₂-phenyl-NCS] | K 100.5 S_B 104.5 [N 47] I | | 0.345 |
| [C₄H₉S-naphthalene-CO₂-phenyl-CN] | K 108.2 N 118.7 I | | |
| [CN-naphthalene-phenyl-C₅H₁₁] | | 4.88 | |
| [C₄H₉O-naphthalene-C≡C-phenyl-NCS] | | 6.21 | |
| [CN-naphthalene-phenyl(CH₃)-C₅H₁₁] | | 2.37 | |
| [C₄H₉S-naphthalene-phenyl-CN] | | 4.11 | |

The n measurements are normalized for 25° C. and were carried out using an Abbe refractometer and using 3 wt % of the compound to be measured in a non-polar eutectic nematic host, typically such as where R and R¹ are alkyl.

Figure 6:
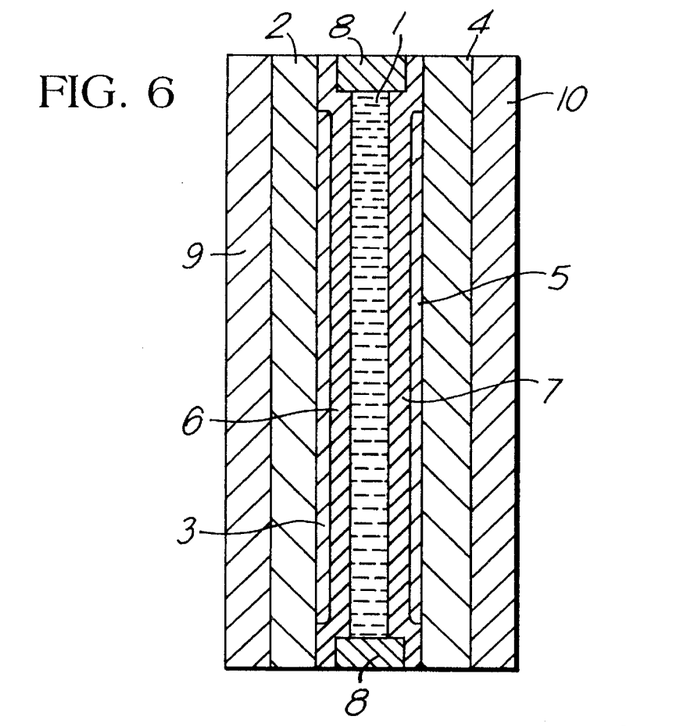
FIGS. 6 and 7 are schematic representations of a liquid crystal device of the invention and a Kerr cell of the invention.

FIG. 6 a liquid crystal cell comprises a layer 1 of liquid crystal material, where the material is a mixture incorporating compounds of formula I, sandwiched between a glass slide 2 having a conducting layer 3 on its surface, e.g. of indium tin oxide, and a glass slide 4 having a transparent conducting layer 5 on its surface. The slides 2,4 bearing the layers 3,5 are respectively coated with films 6,7 of a polyimide layer. Prior to construction of the cell the films 6 and 7 are rubbed with a soft tissue in a given direction, the rubbing directions being arranged parallel to the construction of the cell. A spacer 8 e.g. of polymethylmethacrylate, separates the slides 2,4 to the required distance e.g. 5 microns. The liquid crystal material 1 is introduced between the slides 2,4 by filling the space between the slides 2,4 and spacer 8 and sealing the spacer 8 in a vacuum in a known way.

A polarizer 9 is arranged with its polarization axis parallel to the rubbing direction on the films 6,7 and an analyzer (crossed polarizer) 10 is arranged with its polarization axis perpendicular to that rubbing direction. When a voltage is applied across the cell by making contact with the layers 3 and 5 the cell is switched.

In an alternative device (not shown) based on a cell construction as shown in FIG. 6 the layers 3 and 5 may be selectively etched in a known way, e.g. by photoetching or deposition through a mask, e.g. to provide one or more display symbols, e.g. letters, numerals, words or graphics and the like as conventionally seen on displays. The electrode portions thereby may be addressed in a variety of ways which include multiplexed operation.

Figure 7:
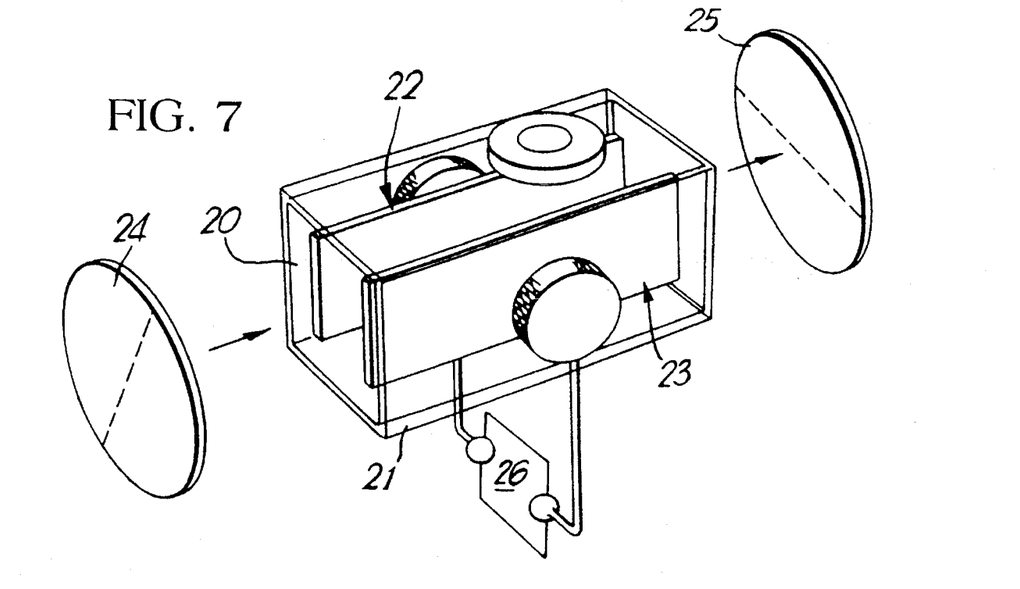

FIG. 7 shows a Kerr cell 20. It comprises a glass cell 21 having two electrodes 22 and 23, which can be filled with a polar isotropic medium such as compounds of formula II or materials comprising mixtures including at least one compound of formula II. The cell 20 can be positioned between crossed linear polarizers 24 and 25, whose transmission axes are arranged to be at ±45° to an applied electric field. Where there is zero voltage across the electrodes 22 and 23, and the cell 20 acts as a closed shutter. The application of a modulating electric field from voltage source 26 generates an electric field causing the cell 20 to act as a variable wave plate and thus operating as a variable aperture shutter where opening is proportional to the electric field.

We claim:

1. A liquid crystalline compound of formula I:

Formula I where A is selected from naphthyl, fluorinated naphthyl, brominated naphthyl, B is thiophene, $R_1$ and $R_2$ containing 1 to 15 carbon atoms are independently selected from the group consisting of alkyl, alkoxy, alkynyl, thioalkyl, Br, CN, SCN, NCS, perfluoroalkyl, perfluoroalkoxy and hydrogen, X is selected from the group consisting of C≡C, COO and C=C, m is 0 or 1, and n is 1.

2. A compound according to claim 1 where at least one of the terminal groups $R_1$ and $R_2$ is selected from the group consisting of alkyl, alkoxy, alkynyl and thioalkyl.

3. A compound according to claim 2 where at least one of the terminal groups is straight chain.

4. A compound according to claim 1 where A is naphthyl.

5. A compound according to claim 4 where m is 0.

6. A compound according to claim 5 where at least one of the terminal groups is alkynyl.

7. A compound according to claim 5 where at least one of the terminal groups is NCS.

8. A compound according to claim 5 where at least one of the terminal groups is CN.

9. A compound according to claim 5 where at least one of the terminal groups is thioalkyl.

10. A liquid crystalline material, being a mixture of compounds, and characterized in that it comprises at least one compound according to claim 1.

11. A material according to claim 10 and further characterized in that it comprises at least one compound of formula IV Formula IV where $R_A$ is selected from CN, alkyl and alkoxy.

12. A material according to claim 10 and further characterized in that it comprises at least one compound of formula V Formula V where $R_1$ is $C_{1-10}$ n-alkyl or n-alkoxyl and the fluorosubstituent(s) can be in any one or two of the available substitution positions.

13. A liquid crystal device characterized in that it uses a material according to claim 10.

14. A device comprising two spaced cell walls each bearing electrode structures and treated on at least one facing surface with an alignment layer, a layer of liquid crystal material enclosed between the cell walls, characterized in that the liquid crystal material contains one or more of the compounds described by claim 1.

15. A device comprising two spaced cell walls, a layer of liquid crystal material in its pretransitional state enclosed between the cell walls, characterized in that the liquid crystal material contains one or more of the compounds described by claim 1.

16. A polymer dispersed liquid crystal layer comprising small droplets of a liquid crystal material dispersed within a matrix of a transparent polymer, characterized in that the liquid crystal material contains one or more of the compounds described by claim 1.

* * * * *

UNITED STATES PATENT AND TRADEMARK OFFICE
CERTIFICATE OF CORRECTION

PATENT NO. : 5,496,500
DATED : March 5, 1996
INVENTOR(S) : TOYNE et al

It is certified that error appears in the above-indentified patent and that said Letters Patent is hereby corrected as shown below:

Column 14, claim 11, delete Formula IV and replace by:

Formula IV

Signed and Sealed this

Twenty-sixth Day of November 1996

Attest:

BRUCE LEHMAN

*Attesting Officer*     *Commissioner of Patents and Trademarks*